United States Patent [19]

Dittmar et al.

[11] Patent Number: 4,825,863
[45] Date of Patent: May 2, 1989

[54] PORTABLE HOT, HUMID AIR INHALATOR FOR COMBATTING HYPOTHERMIA IN HUMANS

[75] Inventors: André Dittmar, Lyons; Jacques Foray, Chamonix; Georges Delhomme, Lyons; Yves Blain, Vaulnaveys Le Haut; Pierre Berard, Chamonix, all of France

[73] Assignee: Centre National De La Recherche Scientifique (C.N.R.S.), Paris, France

[21] Appl. No.: 736,283

[22] Filed: May 20, 1985

[30] Foreign Application Priority Data

May 22, 1984 [FR] France .................................. 84 08190

[51] Int. Cl.[4] ............................................. A61M 16/00
[52] U.S. Cl. ........................... 128/203.27; 128/204.13; 128/204.17
[58] Field of Search ....................... 128/200.11, 200.12, 128/200.14, 203.16, 203.17, 203.23, 203.26, 203.27, 204.17, 204.13; 261/129, 130, 131, 137, 138, 139, 152–157

[56] References Cited

U.S. PATENT DOCUMENTS

| | | | |
|---|---|---|---|
| 1,239,634 | 9/1917 | Stuart | 128/203.26 |
| 1,485,260 | 2/1924 | Ernst | 128/203.27 |
| 1,771,386 | 7/1930 | Wyss et al. | 128/203.26 |
| 2,046,633 | 7/1936 | Johnson | 128/203.27 |
| 2,091,034 | 8/1937 | Duncan | 128/203.26 |
| 2,368,115 | 1/1945 | Chapple | 128/203.27 |
| 3,115,134 | 12/1963 | Schmahl | 128/204.13 |
| 3,695,267 | 10/1972 | Hirtz et al. | 128/203.17 |
| 3,903,883 | 9/1975 | Pecina et al. | 128/203.27 |
| 4,038,980 | 8/1977 | Fodor | 128/203.27 |
| 4,121,583 | 10/1978 | Chen | 128/203.27 |
| 4,288,396 | 9/1981 | Ohestad | 128/204.17 |
| 4,369,777 | 1/1983 | Lwoff et al. | 128/204.17 |
| 4,682,010 | 7/1987 | Drapeau et al. | 128/204.17 |

FOREIGN PATENT DOCUMENTS

| | | | |
|---|---|---|---|
| 074564 | 4/1976 | Australia | 128/203.27 |
| 195028 | 1/1958 | Austria | 128/203.27 |
| 210516 | 8/1960 | Austria | 128/204.17 |
| 0009543 | 4/1980 | European Pat. Off. | 128/201.13 |
| 2162340 | 3/1978 | France | 128/203.17 |
| 133561 | 4/1960 | U.S.S.R. | 128/204.17 |
| 197946 | 4/1924 | United Kingdom | 128/204.17 |
| 526678 | 9/1940 | United Kingdom | 128/203.27 |
| 1424623 | 2/1976 | United Kingdom | 125/204.17 |

Primary Examiner—Edward M. Coven
Assistant Examiner—K. M. Reichle
Attorney, Agent, or Firm—Weingarten, Schurgin, Gagnebin & Hayes

[57] ABSTRACT

A portable unit for combatting hypothermia comprises:
a cylindrical insulating housing (1) opened at both ends,
a heater/humidifier subassembly (20) in the housing,
air circulator (16),
a hose (9) connected to the outlet,
a heat sensor (30) centered in the hose,
and a heater regulator (24).

6 Claims, 3 Drawing Sheets

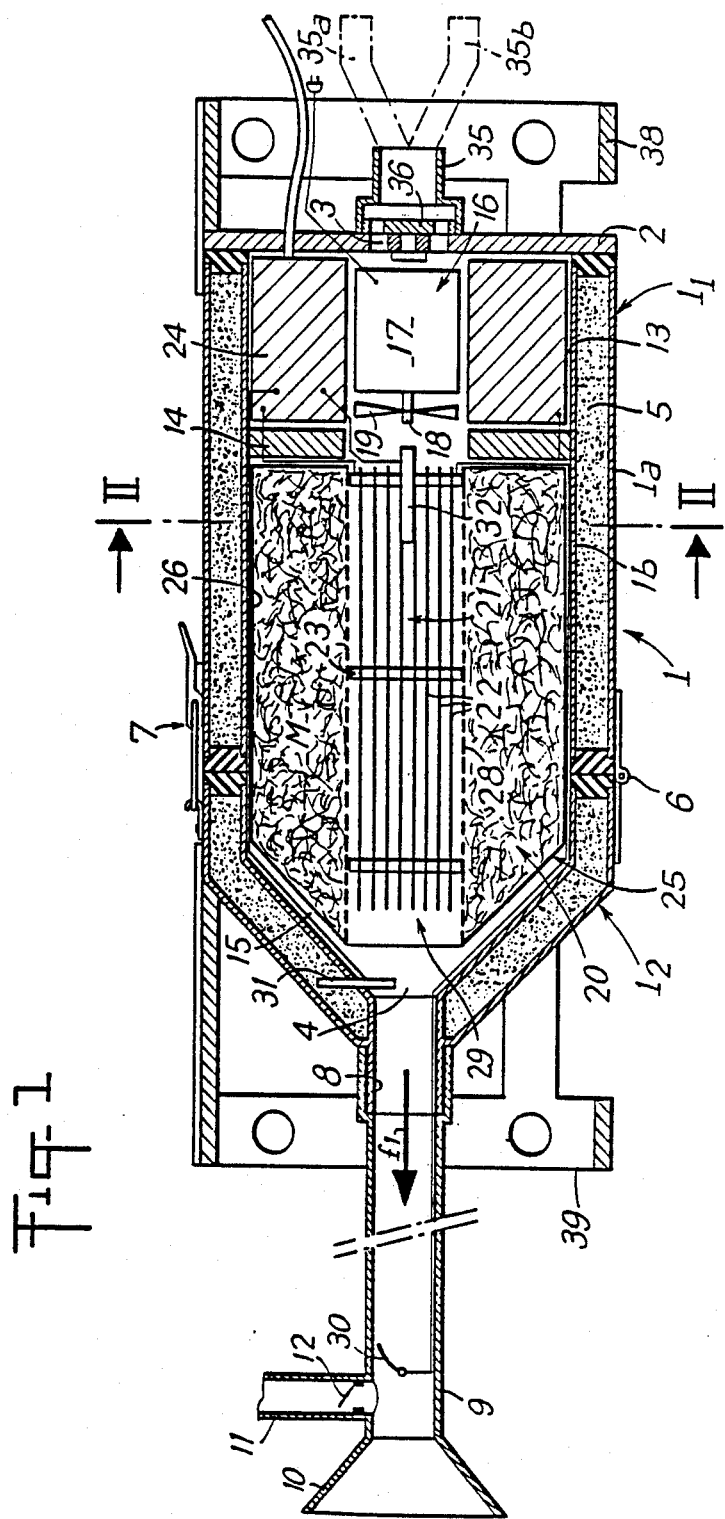

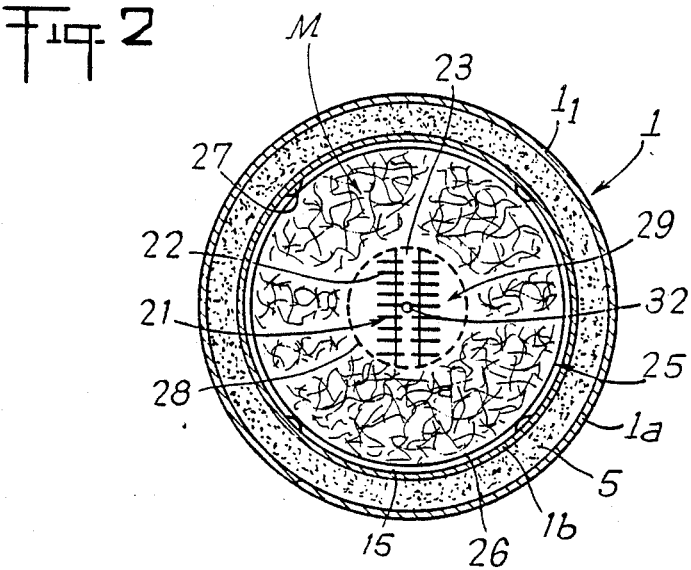
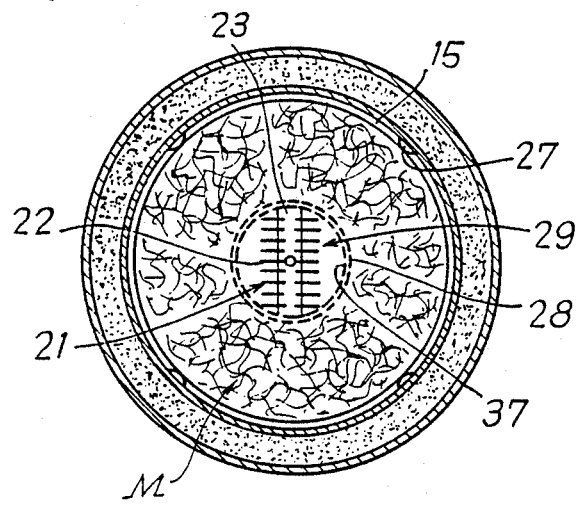

4,825,863

PORTABLE HOT, HUMID AIR INHALATOR FOR COMBATTING HYPOTHERMIA IN HUMANS

BACKGROUND OF THE INVENTION

This invention concerns apparatus for treating hypothermia in humans by hot air inhalation and is mainly addressed to devices which may be qualified as portable and self-contained types, in other words, field units designed for use at the site of an accident.

Experiments have shown the usefulness of supplying heat by pulmonary channels to an accident victim in a state of hypothermia.

Indeed, the human body can be deemed to consist of two main parts in terms of thermal regulation. The most sensitive part or thermal core, is that part the temperature of which is normally maintained at 37° C., said part including the brain, heart, liver and so on. The second part may be considered as peripheral to the first and can tolerate variable temperatures, given the organic functions to be maintained and the capacities for interaction with the body's environment. Said second part basically includes the muscles and limbs.

A significant temperature differential between these two main parts of the human body is thus acceptable, provided the temperature of the thermal core itself does not fall below 30° C.—a temperature below which the heart begins to malfunction and may even stop.

Experiments have shown that heat must mandatorily be provided to the thermal core of the human body to keep the vital organs involved in optimal working order, enabling any localized hypothermia at the perimeter or second part to be countered.

It has been observed that introducing hot air directly through the lungs makes it possible to meet this requirement, provided the hot air is otherwise sufficiently moistened to preclude the risk of bronchial spasms and of drying out of the respiratory channels.

Several solutions have already been proposed in view of providing hot and humid air for this purpose.

One such solution consists in using an external combustion system such as a hotplate or burner to heat a water vessel and produce vapor for inhalation by the patient.

This procedure can be dangerous however, as the vapor cannot be temperature controlled and would burn the respiratory channels.

Moreover, the operation of such a device requires a stable, horizontal position which is often not realizable in practice, since hypothermia usually occurs as the consequence of an accident in a difficult-to-access or obstructed site.

In addition, the use of a burner, commonly involving a store of combustible gas, introduces a hazard which cannot be overlooked.

Another such solution calls upon the exothermal reaction of lime when exposed to water. However, such exothermal reaction does not lend itself to accurate temperature control of the reaction gas and therefore does not meet the stated requirement of supplying a mixture such as humified air at a constant, controlled temperature to place the subject in a receptive, relaxed and expectant state most propitious to the treatment of accident-caused hypothermia.

Besides, the difficulty of practically implementing such an approach in the context of a traffic accident or a mountain rescue operation is obvious. And furthermore, such as approach does not afford the kind of "stand-alone" capability required in practice for the prevention and control of hypothermia.

SUMMARY OF THE INVENTION

The present invention is directed to obviating the drawbacks of the present known means for combatting hypothermia, involving the inhalation of hot, humid air, by providing a portable apparatus with considerable stand-alone capability, usable in any required position.

The main object of the invention is to provide an apparatus enabling efficient delivery, in a wide range of environmental temperatures and atmospheric pressures, of hot, humid air controlled to have an adjustable, maximum temperature being optimal for the purpose of warming a body's thermal core, yet without risk for the respiratory channels.

It is another object of the invention to provide an apparatus which can be easily manipulated by persons not necessarily trained in its use, which is extremely rugged, especially in terms of impact strength.

Still another object of the invention is to provide a compact apparatus able to be introduced, lifted to, engaged in or otherwise placed in any space through which a human body has passed before it, in order to carry out all required rescue operations on a human being experiencing or prone to experience hypothermia as the result of an accident.

The object of the invention is particularly designed to serve as emergency rescue gear in accident situations occuring in mountain country, on roads and highways, or at sea, among other places.

To meet the above-stated objectives the invention provides a portable hypothermia treatment unit comprising:

a basically cylindrical housing, made at least partly of a material having a good thermal insulation coefficient, and having an air inlet at one end and an outlet at the other end;

in said housing, a heater/humidifier subassembly;

in said housing, an air circulating means for running air through the unit;

a hose connected to said air outlet and comprising an endpiece and, upstream from the latter, a vent controlled by a discharge valve sensitive to the air pressure obtaining in the hose;

a heat sensor centered in said hose, near the endpiece thereof;

and regulating means controlled at least by the sensor to meter the heat energy delivered by the unit.

DESCRIPTION OF THE DRAWINGS

Various other features of the invention will become apparent in reading the following description of some illustrative embodiments thereof, with reference to the appended drawings.

FIG. 1 is a sectional elevation of the unit according to the invention.

FIG. 2 is a cross section taken along line II—II of FIG. 1.

FIG. 4 is a cross section identical to that of FIG. 2, except illustrating an alternative embodiment of the invention.

DESCRIPTION OF THE INVENTION

Figure 3:
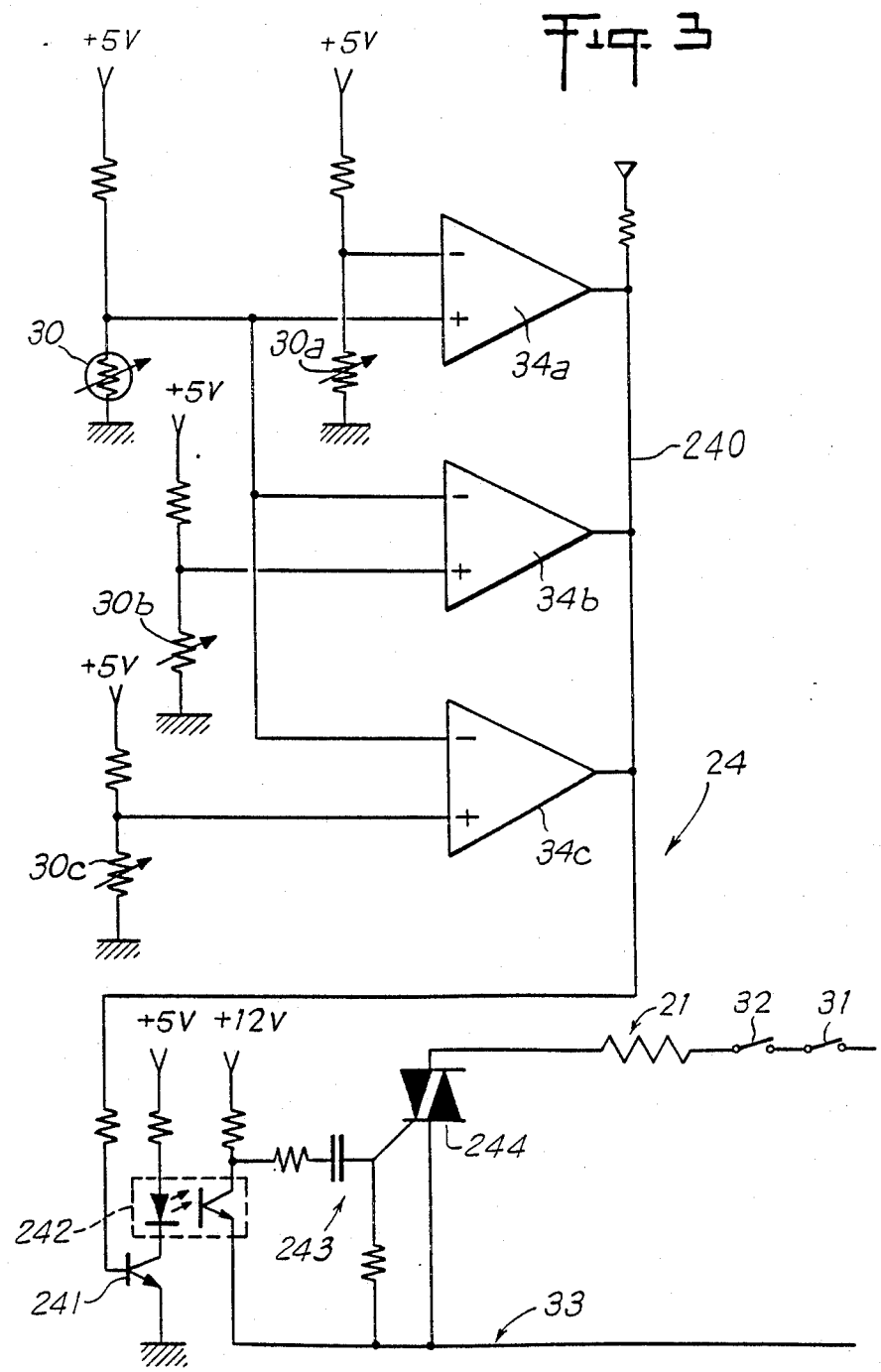
FIG. 3 is a block diagram of one of the components of the invention.

Referring to FIGS. 1 and 2, the unit can be seen to comprise a basically cylindrical housing 1, closed at one end by a wall 2 delimiting an air inlet 3. The other end housing 1 contains the air outlet 4 substantially centered therein.

In one embodiment, said housing 1 consists of two concentric cases 1a and 1b made of a suitably heat insulating, high strength material. The two cases 1a and 1b are joined together by a filler 5 of insulating material, for example an open or closed-cell foam material, the density whereof is selected to contribute to the high strength of the unit as a whole when snugly fitted between the two facing walls of said concentric cases 1a, 1b.

In a prefered construction, the housing 1 comprises a main body $1_1$ and a secondary body or cover $1_2$. Said secondary body or cover $1_2$ is fitted to body $1_1$ by means of a hinge 6 and a suitable fastener 7, such as a toggle.

Cover $1_2$ forms the outlet 4 having a fitting 8 adapted to temporarily or permanently connect with a hose 9 whose free end is provided with a mouthpiece or a face mask 10. Said hose 9 is provided, immediately before endpiece 10, with a bypass or venting means 11 throttled by a discharge valve 12 sensitive to the pressure obtained in hose 9.

Within main body $1_1$ are two compartments, 13 and 15, located respectively against the back inside end wall 2 and in the front, partly within cover $1_2$, and separated by a partial transverse partition 14.

Compartment 13 contains air circulating means 16 such as a fan, to move air taken from the outside of the housing 1 through inlet 3. Said means 16 may consist of an electric motor 17 mounted by any appropriate means, directly or indirectly in end wall 2, and comprising a drive shaft 18 axially centered in housing 1, with a propeller or fan blade 19 to impel air or a gas mixture in the direction of arrow $f_1$ through partition 14 and into compartment 15. Motor 17 is preferably supplied with electric current from an outside power source to which the emergency unit is connected via a power cord.

In certain cases, compartment 13 can be designed large enough to house a self-contained power source such as a rechargeable battery.

Compartment 15 contains a heater/humidifier subassembly 20. Said subassembly 20 includes a bundle 21 of electrical resistance elements 22, preferably of the blade type, held parallel to one another by brackets 23, as shown in FIGS. 1 and 2. Bundle 21 extends coaxially to the axis of housing 1 at least part of the length of compartment 15. Said bundle is electrically connected to regulating means 24 controlling the supply of power to the resistance elements from the internal or external electrical power source. Said regulating means 24 is preferably given an annular shape adapted to be arranged within compartment 13, around said air circulating means 16.

Subassembly 20 further comprises an annular humidifier cartridge comprising a cylindrical outside wall 26 the outside diameter whereof is designed to fit snugly into compartment 15. To this end the inside perimeter wall of compartment 15 can be provided with axial ribs 27 for cartridge centering and holding purposes. Humidifier cartridge 25, in addition to its outside wall, comprises a cylindrical inside wall 28, concentric with said outside wall 26, which bounds a hollow center 29 serving as both a duct for the flow of air impelled by means 16 and an accommodation for resistance bundle 21. Inside peripheral wall 28 is of openwork construction such as of wire mesh, expanded metal, perforated sheet or plate, or similar material.

Peripheral walls 26 and 28 are joined by transverse walls establishing an annular space filled with a mass M of fibrous or similar compound having a marked hydrophilic character. For example, said compound or material M can consist of cellulose fiber rovings.

Humidifier cartridge 25 is shaped to fill the internal volume of compartment 15 such as to be able to be axially immobilized within the latter, between partition 14 and the inside wall of cover $1_2$, which walls could, though not so-drawn in the figure, be provided with limit bosses or, preferably, projecting pads of a resilient material for cushioning purposes.

The regulating means 24, particularly illustrated by the block diagram of FIG. 3, is adapted to respond to a heat sensor 30. In the hypothermia treatment unit according to the invention, this sensor 30 is disposed in the center of hose 9, near endpiece 10 and, in any case, slightly upstream from venting bypass 11. Said regulating means 24 is also controlled by a first thermostat 31 located in compartment 15 to monitor the temperature of the air leaving subassembly 20 through hose 9, and by a second thermostat 32 monitoring the heat output of resistance bundle 21 in center accommodation 29.

Thermostats 31 and 32 are series connected in the resistance bundle 21 power supply circuit 33 controlled by regulating means 24. Said means 24, as shown in FIG. 3, comprise adjustable potentiometers 30a, 30b and 30c, associated with comparators 34a, 34b and 34c, the latter being included as a safety consideration, to maintain the electrical continuity of the link between the heat sensor 30 and the power supply circuit 33 opening and closing means. More particularly, the comparators 34a, 34b, 34c, connected in a well-known wired-OR arrangement, are coupled over link 240 to a transistor switch 241 that, in turn, is coupled to a triac 244 via a RC network 243 in series with an electro/optical coupling illustrated by a dashed box 242. The comparators 34a, 34b, 34c are each operative to controllably drive the transistor switch 241 to its off condition, and therewith the triac 244, to de-energize the heating element 21, respectively in response to the heating of the air over its setpoint temperature, a break in link 240 continuity, and in response to comparator 34a malfunction.

It should be understood that said regulating means 24 could be made in any other equivalent way within the competence of persons skilled in the art.

The operation of the afore-described inhalator unit will now be described.

At power-up, air circulating means 16 drive intake air in the direction of arrow $f_1$, through compartment 15. Turning the unit on also closes circuit 33 causing power to flow to the resistance elements 22 of bundle 21. The air driven by means 16 goes through the bundle 21 and becomes heated before flowing into hose 9.

Heating of bundle 21 causes the water retained in the material M of cartridge 25 to evaporate through the openwork peripheral wall 28 and into flow channel 29 such that the heated air picks up water vapor before flowing into hose 9.

The heated, humidified air is kept at a constant temperature by sensor 30 acting on regulating means 24. Thus, the hypothermic subject can inhale through endpiece 10, air having a constant temperature regulated according to the heat supply required, to the specific state of hypothermia at hand and to the chosen parameters as adjusted by means of potentiometer 30a.

The air in hose 9 is kept at a constant temperature thanks to heat sensor 30, regardless of the heat loss which may occur along the length of said hose due to varying operating conditions. Hot, humid air output in excess of that actually used by the patient is discharged through bypass 11 which can serve either merely to vent the unit to the atmosphere or to route said excess air to heat the patient's "peripheral" body part or limb part.

During operation of the unit, evaporation in the layers of hydrophilic material M nearest the resistance bundle 21 causes the water retained in the peripheral or outside layers to migrate radially towards the inside. This results in gradual water loss enabling a substantially constant rate of evaporation to be maintained, thus providing humified hot air with a fairly constant hygrometry.

The arrangement of cartridge 25 around bundle 21 enables giving the material M an additional role of heat insulation to reduce radial heat loss in conjunction with the insulating nature of housing 1.

It deserves to be emphasized that air flow means 16 and regulating means 24 are placed between the inlet 3 and subassembly 20 such that said means 16 and 24 are not subject to heating during unit operation or to thermal stresses likely to adversely affect their operation, especially over time.

Inlet 3 preferably carries a fitting 35 equipped with a throttling plug 36. Fitting 35 is adapted to either aspirate air directly from the outside environment, or to be connected to a source of a gas mixture suitable for the required treatment.

As shown in FIG. 1, fitting 35 can also carry two tubes 35a and 35b enabling the two options just mentioned to be combined, for simultaneous intake of fresh air and of a complementary gas mixture supplied by an auxiliary tank.

It can be seen, by comparing FIG. 4 with FIG. 2, that the inside peripheral wall 28 of cartridge 25 can be associated with a sleeve 37, movable either axially or angularly, in such a way that it may have its openings fully or partially coincide with the openings of the wall 28 by respectively moving the sleeve 37 relative to the wall 28 either in a direction defined along the direction of its length or about an arc defined by the rotation of the sleeve about its central longitudinal axis. Such a sleeve can serve to adjust the interface area between cartridge 25 and flow channel 29, making it possible to preset the rate of humidification for the hot air output and, if required, to thus affect the unit's operating life.

Housing 1 has been defined in the foregoing to consist of two parts, making for easier insertion and replacement of humidifier cartridge 25. It can also be envisaged to provide the housing 1 with a filler hole making it possible to recharge the cartridge from an external water supply.

Referring again to FIG. 1, the main body $1_1$ and the secondary body or cover $1_2$ can be seen to carry extension parts which are in fact ring handles 38 and 39, also serving to protect end fittings 35 and 8.

It should be clear from the foregoing description that the means implemented in the invention provide a compact, portable apparatus, able to deliver hot air at a controlled temperature, and at a substantially constant humidity.

The structural design of the invention moreover makes the unit suitable for use in any position, whilst being either partially or wholly self-contained, depending on whether the electrical power required for its operation is taken from an external or a built in power source.

In addition, the unit's output is independent of environmental temperature and pressure factors. And furthermore, the thermal insulation provided by the construction of the housing and the concentric arrangement of humidifier cartridge 25 in relation to resistance bundle 21 makes it possible to produce suitably humidified and temperature controlled hot air during a considerable amount of time, even under very severe operating conditions, without adjusting the unit's operation.

The invention should not be construed to be limited by the embodiments described and illustrated herein, as various modifications may be made without departing from the scope and spirit of the invention.

What is claimed is:

1. A temperature controlled portable respiratory appliance for providing in-the-field hypothermia treatment; comprising:
    an axially-extending generally-cylindrical insulated housing having a generally cylindrical main body portion defining an inlet and a generally cylindrical cover portion defining an outlet, said inlet and outlet being coaxial with the axis of said housing, said main body portion having an internal radially extending partition that divides the housing into first and second axially-spaced compartments, said first compartment located between the inlet and the partition and the second compartment located between the outlet and the partition, said partition including an opening which is coaxial with the axis of said housing such that said compartments are in fluid communication with each other and said housing defining an axial path between said inlet and said outlet, via said opening;
    air circulating means mounted into said first compartment in said main body portion of said cylindrical insulated housing in fluid communication with said inlet for impelling air from the inlet to said outlet along said axial path through said housing;
    a heater/humidifier subassembly, including an annular hydrophilic cartridge having an inside generally-cylindrical wall defining a hollow, generally-tubular core, said cartridge being slideably mounted in said second compartment of said housing in such a way that said core is co-axially aligned with said axial path and said cartridge being slideably removable from said housing, said inside cylindrical wall of said annular cartridge having radial openings for intercommunicating said hydrophilic cartridge and said hollow core;
    said heater/humidifer subassembly further including a bundle of electrical resistance elements mounted within said hollow core and extending through at least a part of the length of said hollow core;
    a hose having two ends and connecting to said outlet at one end;
    mouthpiece means connected to said hose at the other end;
    mouthpiece bypass means connected to said hose upstream from the mouthpiece means;
    air temperature sensor means mounted in said hose at a point upstream from said mouthpiece bypass means; and regulating means mounted in said first compartment in said main body portion of said housing and coupled to said electrical resistance elements and to said air temperature sensor means for controlling the energization of said electrical resistance elements in response to the temperature sensed by said air temperature sensor means;

and wherein said regulating means is annular in form and surrounds said air circulating means.

2. The respiratory appliance according to claim 1, further including a first and second thermostat means, said first themostat means located in said housing near said outlet and said second thermostat means located within said resistance elements, wherein said regulating means also being coupled to said first thermostat means and to said second thermostat means.

3. The respiratory appliance according to claim 1, wherein said resistance elements are blade type elements extending in parallel relation to each other and the axis of said housing.

4. The respiratory appliance according to claim 1, wherein said housing consists of two concentric cases defining an annular space therebetween and a filling material therebetween having a good thermal insulation coefficient.

5. A temperature controlled portable respiratory appliance for providing in-the-field hypothermia treatment; comprising:

an axially-extending generally-cylindrical insulated housing having a generally cylindrical main body portion defining an inlet and a generally cylindrical cover portion defining an outlet, said inlet and outlet being coaxial with the axis of said housing, said main body portion having an internal radially extending partition that divides the housing into first and second axially-spaced compartments said partition including an opening which is coaxial with the axis of said housing such that said compartments are in fluid communication with each other and said housing defining an axial path between said inlet and said outlet, via said opening;

air circulating means mounted into said first compartment of said cylindrical insulated housing in fluid communication with said inlet for impelling air from the inlet to said outlet along said axial path through said housing;

a heater/humidifier subassembly, including an annular hydrophilic cartridge having a closed peripheral wall, an inside generally-cylindrical wall of openwork construction defining a hollow, generally-tubular core and a body of hydrophilic material therebetween, said cartridge being slideably mounted in said second compartment of said housing in such a way that said core is co-axially aligned with said axial path and said cartridge being slideably removable from said housing, said openwork inside cylindrical wall of said annular cartridge defining radial openings for intercommunicating said hydrophilic cartridge and said hollow core;

said heater/humidifier subassembly further including a bundle of electrical resistance elements mounted within said hollow core and extending through at least a part of the length of said hollow core;

a hose having two ends and connected to said outlet at one end;

mouthpiece means connected to said hose at the other end;

mouthpiece bypass means connected to said hose upstream from the mouthpiece means;

air temperature sensor means mounted in said hose at a point upstream from said mouthpiece bypass means; and regulating means mounted in said first compartment of said housing and coupled to said electrical resistance elements and to said air temperature sensor means for controlling the energization of said electrical resistance elements in response to the temperature sensed by said air temperature sensor means.

6. The respiratory appliance according to claim 5, further including an annular sleeve, also having radial openings, slideably mounted within said hollow core between said resistance elements and said cartridge and coaxial with the axis of said housing such that openings within said sleeve at least partially coincide with openings within said peripheral wall, for movement in an axial or angular direction to adjust the interface area between the cartridge and the axial path.

* * * * *